United States Patent [19]

Turner et al.

[11] Patent Number: 4,817,603

[45] Date of Patent: Apr. 4, 1989

[54] LANCET DEVICE

[75] Inventors: Robert C. Turner; Rury R. Holman, both of Oxford, England

[73] Assignee: Glyme Valley Technology Limited, Woodstock, England

[21] Appl. No.: 79,381

[22] Filed: Jul. 30, 1987

[30] Foreign Application Priority Data

Jul. 30, 1986 [GB] United Kingdom ................. 8618578

[51] Int. Cl.$^4$ ............................................. A61B 17/34
[52] U.S. Cl. .................................. 128/329 R; 604/136
[58] Field of Search ................... 128/329 R, 314, 315; 604/130, 136, 137, 138, 156, 157, 193, 196

[56] References Cited

U.S. PATENT DOCUMENTS

| | | | |
|---|---|---|---|
| 2,704,072 | 3/1955 | Sarnoff ................................. | 604/138 |
| 2,832,339 | 4/1958 | Sarnoff et al. ...................... | 604/138 |
| 3,543,603 | 12/1970 | Giley .................................... | 604/138 |
| 3,584,626 | 6/1971 | Johansson ............................ | 604/193 |
| 3,612,051 | 10/1971 | Arce ..................................... | 604/157 |
| 4,226,235 | 10/1980 | Sarnoff et al. ...................... | 604/136 |
| 4,375,815 | 3/1983 | Burns . | |
| 4,388,925 | 6/1983 | Burns .............................. | 128/329 R |
| 4,416,279 | 11/1983 | Lindner et al. ................. | 128/329 R |
| 4,484,910 | 11/1984 | Sarnoff et al. ...................... | 604/157 |
| 4,577,630 | 3/1986 | Nitzsche et al. . | |
| 4,723,937 | 2/1988 | Sarnoff et al. ...................... | 604/136 |

FOREIGN PATENT DOCUMENTS 0081665  6/1983  European Pat. Off. .

Primary Examiner—John D. Yasko
Attorney, Agent, or Firm—Millen & White

[57] ABSTRACT

FIG. 2 shows a lancet device for performing a pricking operation. A barrel (36) is closed at one end by a finger guard plate (43) having a centrally positioned hole (42). Prior to use, the hole (42) is closed by a centrally disposed axially protruding spigot (54) found on the inside of a cap 40. In use, the cap is removed and the spigot (54) is inserted into the other end of the barrel (36) to bear against a shank 44 of a needle assembly 16 is secured to the periphery of a hole (46) in an end plate (48). A finger to be pricked is placed against the finger guard plate (43) and a thumb is placed over the cap (4) which is now located over the other end of the barrel from that shown in the drawing.

Pressure between the thumb and finger causes the spigot (54) to break the attachment between the shank of the needle and the periphery of the hole (46) to allow the needle assembly to be projected through the barrel (36) under the force exerted by a compressed spring (16).

A needle (34) of the assembly projects through the hole (42) to prick the finger, before being retracted into the barrel (16) as a result of the spring (16) having overstretched itself past its null position.

10 Claims, 3 Drawing Sheets

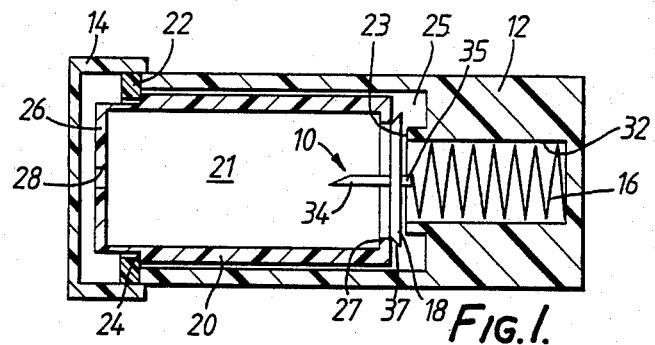
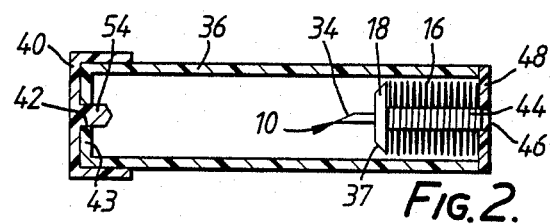
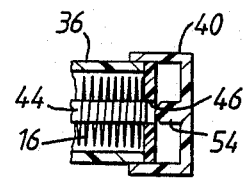
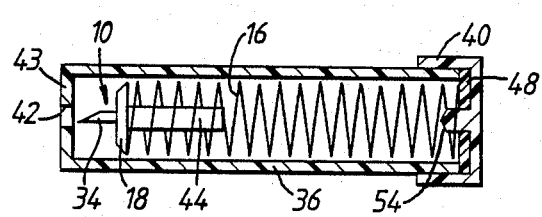

4,817,603

LANCET DEVICE

BACKGROUND OF THE INVENTION

This invention relates to a lancet device for performing a pricking operation, for example for use in taking skin capillary blood samples.

In the case of certain diseases such as diabetes, the patient is required to provide regular small specimens of blood, which are sent for analysis in a specially designed carrier tube. This involves pricking a finger or other suitable part of the anatomy in order to obtain the blood specimen. It is physically and psychologically difficult for many people to prick their own finger with a hand held needle, which must be sterile, and an object of the invention is to provide a simple hand-held automatic lancet device to facilitate this task.

British patent specification No. 1 599 654 dated May 26, 1978 in the name of the present applicants describes a hand held device in which a holder has a resiliently biased arm to the end of which a lancet needle is inserted. The arm is able to occupy a retracted position or an operative position in which the needle extends through a finger guard to prick a finger. The finger guard and needle both have to be separately detached from the holder after each pricking operation has been performed and replaced by a sterile guard and needle if the required sterile conditions are to be maintained between successive pricking operations. The separate replacement of the guard and needle is time consuming, and the needle is exposed to the ambient surroundings prior to pricking of the finger which may detract from the sterile conditions of the pricking operation.

SUMMARY OF THE INVENTION

According to the present invention, a lancet device comprises a housing within which is located firable biassing means arranged to act on a needle assembly, there being a outlet aperture in the housing through which a needle secured to the said assembly will be driven by the said baissing means on firing of the biassing means, means being provided to halt the needle assembly so that the needle cannot extend beyond the aperture beyond a predefined distance. Preferably means are provided to automatically retract the needle back through the aperture into the housing after it has passed through the said aperture. The means to automatically retract the needle are preferably afforded by the firable biassing means. The firable biassing means may conveniently comprise a spring attached to the needle assembly and so sized in relation to the housing as to be capable on firing of driving the needle through the aperture to an operating position in which position the said spring is over extended and then to be capable on returning to its null or resting position of retracting the needle back into the housing. Alternatively, or in addition the means to automatically retract the needle may comprise a return spring or biassing means separate from the firable biassing means.

The needle assembly preferably comprises an incision forming needle carried on a transverse base plate or member. With such device the needle is positioned inside the housing in a sterile environment until the actual pricking operation is performed. The device is simple in construction as it does not require the needle to be mounted on an arm. The device is also cheap to manufacture and so part or all of the device may be disposed of after use.

In one form of the invention the housing comprises an actuator portion telescopically mounted within a barrel portion, the aperture being located in the actuator portion.

The base of the needle assembly may be held in a cocked position of the device prior to firing of the biassing means by stop means at or adjacent to the inner end of the actuator.

The biassing means are preferably disposed between the base of the needle assembly and the inner end of the barrel and are attached thereto.

In a modification the needle assembly may be located in a needle holder to which the biassing means are attached.

The firing of the device is preferably achieved by inwards movement of the actuator relative to the barrel beyond the cocked position. This enables the device to be fired, or cocked and fired, merely be a single application of pressure as between finger and thumb. One convenient firing mechanism is provided by one form of the invention in which the actuator at its inner end and the base of the needle at its periphery carry mutually engagable distortable configurations such that whilst they co-operate to hold the biassing means loaded, further manually applied pressure is sufficient to cause one to ride past the other and release the needle assembly for movement down the actuator and out through the aperture under the action of the biassing means.

In another form of the invention a different firing mechanism is provided and in this form of the invention the base of the needle assembly is detachably secured to the actuator adjacent its inner end and the inward movement of the needle assembly or a holder in which it is located is limited by a stop positioned so as to cause the biassing means to be fully loaded when the needle assembly or the holder engages such stop, but which stop is also such as to permit further inward movement of the actuator whereby further manually applied pressure will free the needle assembly from the actuator and release the needle assembly for movement down the actuator and out through the aperture under the action of the biassing means.

In another simpler form of the invention the housing is elongate and opposite the wall having the aperture, there is a second apertured end wall to which the needle assembly is detachably secured by means detachable from outside the housing, the biassing means being located in their fully loaded condition between the needle assembly and the said second end wall.

The needle assembly may have an actuatable member or shank extending in non interfering manner past the biassing means to the second end wall where it is detachably secured.

The second end wall preferably has a central aperture in which the said shank is secured.

A cap having a central spigot of a size appropriate for insertion in the aperture in the second end wall to release the shank therefrom is preferably provided to seal the outlet aperture end prior to use of the device. With this arrangement the outlet aperture is covered by the cap prior to the use of the device to keep the needle sterile. The cap is then conveniently used to operate the lancet device by inserting the spigot in the aperture in the second end wall. The shank of the needle is preferably recessed in the aperture so that accidental release of the needle from the retracted position is substantially prevented. The needle assembly is located within the actuator, the inner end of the inside surface of the actuator and the periphery of the base plate of the needle assembly being provided with co-operating configurations to ensure that the needle assembly cannot fall out of the actuator, the actuator affording the outlet aperture from the housing.

The base plate of the needle at or adjacent its periphery is preferably detachably sealed to the inside of the actuator by a continuous seal. This arrangement allows the needle and actuator portion of the device to be handled as a disposable cartridge which can be sealed to keep the needle sterile, whereas the barrel portion is reusable.

In this embodiment the disposable cartridge may be replaced between successive pricking operations while the re-usable portion may be retained as neither the used needle nor the hole through which the needle extends in the operative position have contacted and possibly contaminated the re-useable portion. Preferably a removable cap is provided to cover the outlet aperture in the actuator to protect the region surrounding the outlet and the needle from contamination before use.

The outlet aperture is preferably sealed prior to use by removable sealing means.

The removable sealing means may comprise a reusable cap frangibly sealed to the housing, the actuator or the barrel, so that the seal can been seen to be intact prior to use but the cap can be used to close the outlet aperture after use prior to disposal of the used device.

Preferably the removable cap is secured to the housing by heat sealing or ultra-sonic welding. This helps to keep the inside of the housing sterile prior to the use of the device. The invention thus also extends to a disposable cartridge assembly for such a two portion lancet device, the cartridge comprising a needle assembly having a needle, a transversely disposed base plate and a shank, the needle assembly being located within an elongate actuator adapted to be slidably telescopically mounted within the barrel portion of the lancet device, the actuator having a centrally disposed outlet aperture at one end, the needle assembly being located at the inner end of the actuator, the inner end, the inside surface of the inner end of the actuator and the periphery of the base plate of the needle assembly being provided with co-operating configurations to ensure that the needle assembly cannot fall out of the actuator.

The base plate adjacent its periphery but preferably not at its periphery is preferably detachably sealed to the inside of the actuator by a continuous seal.

The outlet aperture is preferably sealed prior to use by removable sealing means.

The removable sealing means preferably comprise a reusable cap frangibly sealed to the actuator so that the seal can be seen to be intact prior to use and the cap can be used to close the outlet aperture after use prior to disposal of the used device. Thus the device may also include a second spring which is adapted to be compressed when the needle is in the operative position. The second spring may act to, or assist in, ensuring the retraction of the needle into the housing from the operative position. The second spring may be a sliver of plastics formed in a raised position inside the finger guard or on the needle base plate or may be a complete spring in its own right.

BRIEF DESCRIPTION OF THE DRAWINGS

The invention may be carried into practice in various ways and three embodiments will be described by way of example to illustrate the invention with reference to the accompanying drawings in which:

FIG. 1 is a longitudiual cross-section through a lancet device according to a first embodiment of the present invention with a lancet needle in a retracted position;

FIG. 2 is a view similar to FIG. 1 of a lancet device according to a second embodiment of the present invention;

FIG. 3 is a view similar to FIG. 1 of the right hand or spring end of the lancet device shown in FIG. 2 showing how the lancet needle is released from the retracted position by the cap;

FIG. 4 is a view similar to FIG. 1 of the device shown in FIG. 2 with the lancet needle released from the retracted position;

DESCRIPTION OF THE PREFERRED EMBODIMENTS

Figure 5A:
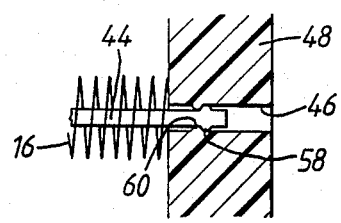
FIGS. 5A and 5B show a third embodiment of the present invention which differs from those shown in FIGS. 1 to 5 in its method of holding the lancet needle in, and releasing the lancet needle from, the retracted position.

The disposable finger pricker shown in FIG. 1 consists of a cylindrical outer housing or barrel 12 closed at one end which affords an inwardly facing relatively narrow diameter well 32 in which is housed a compression spring 16. This well 32 opens out into an actuator chamber 21 and an annular stop wall 23 extends out into the chamber 21 from the end of the well 32 leaving an annular space 25 between its outer surface and the inner surface of this end of the actuator chamber 21.

The other end of the housing 12 is closed by a removable cap 14 which prior to use of the device is preferably secured in place by a frangible seal. This will be described in more detail below.

A hollow cylindrical actuator 20 is slidingly located within the actuator chamber 21. The end of the actuator facing the cap 14 is provided by a finger guard plate 26 having a central aperture 28 (through which the needle moves in use to prick the user's finger). The outer wall of the actuator adjacent this end is provided with an axially facing annular stop or stepped edge 24. The other end of the actuator has an inwardly facing ammular flange 27.

The inside diameter of the flange 27 is greater than the external diameter of the stop wall 23 so that on inward movement of the actuator 20 within the housing 12 the flange 27 can slide freely into the annular space 25.

A needle assembly 10 consisting of a needle 34 disposed towards the hole 28, a transversely disposed base 18 and a shank 35 is secured prior to use between the actuator flange 27 and the end of the stop wall 23. The periphery of the base plate 18 has a chamfer 37 facing towards the cap end of the device. This chamfer is about 45°. The spring 16 is secured to the shank 35 and is sized so that in its uncompressed state or resting position the end of the needle 34 is located within the actuator 20 i.e. to the right of the hole 28 in FIG. 1. The spring is also sized so that on release from its compressed position shown in FIG. 1 it will drive the needle assembly up into contact with the finger guard 26 so that the left hand face of the base plate 18 is brought into contact with the right hand face of the finger guard 26 and the needle will penetrate fully into the flesh being pricked.

The guard 26 acts as the means to halt the needle assembly so that the needle cannot extend beyond the aperture by more than a predefined distance. This predefined distance is determined by the length of the needle and the thickness of the finger guard. Clearly the size of the base plate of the needle assembly should be greater than the size of the aperture, and in order to ensure ready retraction of the needle the size of the aperture should be somewhat larger than the diameter of the needle.

Dimensions, shapes and structures other than those shown for the flange 27 and the chamfer 37 can be used so long as simple retention of the needle assembly on manufacture, shipping and storage of the device is achieved. in combination with simple release of the spring assembly by easy, though deliberate, manual pressure, compressing the actuator into the barrel 12, as between finger and thumb.

In all the embodiments the base of the needle assembly is shaped so as not to significantly with the free movement of the needle down the apparatus and out through the hole 28 with engagement with the finger. Thus if the base is formed as a plate it should have such dimensions or apertures or cutouts as to obviate any significant air piston effect which might interfere with the operation of the device.

Thus the base 18 is preferably in the form of a cross or series of radial arms such that air can travel freely past it and it does not act as a piston or compression disc when the device is operated.

Such radial arms are however of sufficient length to keep the needle assemby centred in the device preventing any significant movement of the needle away from the central longitudinal axis.

The actuator is preferably made of low density polyethylene; the flange 27 may be 1 mm thick and of 1.5 mm radial extent, and its end may engage the chamfer about 0.5 mm radially in from the periphery of the base 18. The base is preferably of acetyl resin and about 2 mm thick and of cross shape, the arm being about 2 mm wide. The needle assembly 10 and spring 16 are held cocked whilst stored by a retaining end ring 22 which is secured to the open end of the barrel 12 and extends inwardly to the inner wall of the actuator chamber so as to engage the stepped axial face 24 on the actuator 20, whereby the flange 27 holds the base 18 of the needle assembly against the action of the spring 16.

Assembly of the device is simply achieved by sterilisation in conventional manner, eg with gamma radiation or ethylene oxide, and then securing the spring 16 to the shank 35 of the needle assembly, locating the spring in the well 32, sliding the actuator into the actuator chamber, making certain the flange 27 secures the needle assembly in position with the spring under compression, securing the retaining ring 22 in position and then securing the end cap in position with a frangible seal to the end ring 22, or the outer wall of the barrel 12, or to both. If the cap, the end ring and the barrel are made of compatible plastics, this sealing can readily be a heat seal as can the sealing of the retaining ring to the barrel 24.

The device is used by breaking the frangible seal (which assures the user that the device is unused and sterile), removing the cap 14, holding the device with a finger to be pricked positioned over the end plate 26, and compressing the device axially until it "fires". The compression causes the flange 27 to ride past the chamfer 37 by virtue of the resilience of the flange 27 and/or the base 18 into the space 25, thus releasing the needle assembly, which is driven by the spring up into contact with the end plate 26, as described above, the needle 34 pricking the finger through the hole 28. The now overextended spring then withdraws the needle 34 back into the actuator where it cannot prick anything. The cap 14 can then be replaced and the used device incinerated or otherwise disposed of.

It will be appreciated that many modifications can be made to the device. Thus it need not be cylindrical, though with other cross sections it will still be desirable for the device to be symmetrical about its longitudiual axis.

The end ring 24 is not essential though it is desirable. Thus the cap 14 could be relied upon to hold the device assembled during storage, the actuator could be a tight sliding fit in the actuator chamber so as to prevent it falling out on removal of the cap prior to use, and the axial compression of the device could be arranged not only to achieve the spring release or "firing" of the device but also the "cocking" of the device i.e. the compression of the spring could be achieved by the user during use rather than being carried out during manufacture of the device. Instead of the firing of the device being achieve by the flange 27 riding past the chamfer 37, the flange 27 could break off the chamfer 37. The retaining ring 22 need not be a ring but could be a number of welded-on spots or even deformed or turned-in portions of the barrel 12. The flange 27 need not be continuous but could be a number of inwardly disposed members fingers or part arcuate flange portions appropriately sized to carry out their above defined function. Conversely the base 18 can be discontinuous as mentioned above though for certainty of assembly it is probably prudent for one or other of base 18 and flange 27 to be continuous.

Equally, the chamfer 37 need not be on the base 18 but could be on the flange 27.

The second embodiment of the invention shown in FIGS. 2 to 4 is a simple structure operating in a similar manner but having a different firing mechanism.

In this embodiment, the barrel 36 is a simple cylindrical tube having the firing mechanism at one end and closed at the other end by a finger guard plate 43 having a central hole 42. Prior to use this hole is closed by a centrally disposed axially protruding spigot 54 formed on the inside of a cap 40. The cap 40 is a tight fit on the barrel 36 and is heat sealed thereto as for FIG. 1. The firing mechanism is located within the end of the barrel 36. This mechanism consists of a needle assembly similar to that in FIG. 1 having a needle 34, a transverse base 18, and a spring 16 acting on the base 18. (The base 18 is shown as having a chamfer 37 as in FIG. 1, but this is not necessary in this embodiment. As discussed for the embodiment of FIG. 1, the base 18 should be shaped so as not to interfere with operation of the device on firing.) The shank 44 of the needle assembly is however much longer than the shank 35 in FIG. 1 and performs the important function of being the portion which is engaged to "fire" the spring. Thus the firing mechanism also includes an end plate 48 to which the shank 44 is detachably secured in such a way that detachment of the shank 44 from the end plate 48 can be achieved from outside the device. This is achieved specifically in this embodiment by providing the end plate 48 with a central hole 46 and securing the shank 44 to the inside face of the plate 48 or partly within the hole 46 e.g. by heat sealing, adhesives or ultra sonic welding. The end plate 48 is secured to the open end of the barrel 36. The dimensions of the spring 16 and the shank 44 are arranged to achieve the same spring function as described for FIG. 1 on release of the spring compressed between the base plate and the end plate 48 on detachment of the shank 44 from the end plate. This detachment is achieved by use of the cap 40 as shown in FIG. 3. The spigot 54 of the cap 40 is located in the hole 46 and pushed into the hole as by pressure between finger and thumb and this breaks the weld between the shank 44 and plate 46, "firing" the spring 16. The holes 42 and 46 are of substantially the same diameter. FIG. 4 shows the null position of the spring after use of the device. The cap 40 can be replaced with the spigot 54 in the hole 42 and the device safely disposed of.

Again the arrangement is clearly capable of being modified in many ways. As mentioned above the cross section need not be cylindrical and the base 18 need and indeed should only be a loose sliding fit in the barrel 36 if it is not provided with apertures or cutouts. The firing mechanism need not involve the securement of the shank 44 directly to the end plate 46 though this is a very simple arrangement. The shank could be secured to a member, e.g. within a tube, depending from the inside face of the end plate 48 or it could be secured to a plate disc or other member located freely outside the end plate 48 and removable e.g. adhesively or frangibly from the shank 44 either by use of the spigot 54 or otherwise.

Figure 5B:
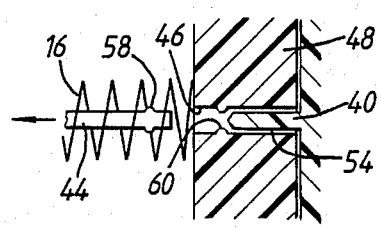

In a modification, of the embodiment of FIGS. 2 to 4, shown in FIGS. 5A and 5B, instead of the shank 44 of the needle assembly being heat sealed or ultra sonically welded to the end plate, the shank 44 extends into the hole 46 of the end plate and is prevented from leaving the hole 46 under the force of the spring 16 by a rim 58 on the shank 44 which bears against an inward deformable rim 60 in the hole 46 as shown in FIG. 5A. In this embodiment, the mechanism is fired by the spigot 54 by pushing the rim 58 on the shank 44 past the rim 60 in the hole 46 to allow the needle assembly to travel under the action of the spring 16 as shown in FIG. 5B.

Figure 6A:
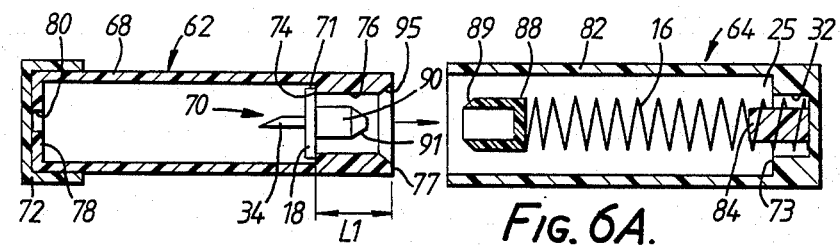
FIGS. 6 (A) to (D) are longitudiual cross-sections through the third embodiment of the present invention showing, sequentially, the assembly, firing and disassembly of the lancet device.

The third embodiment of the invention shown in FIGS. 6A to 6D is a device in which a portion 64 housing the firing mechanism is reusable and a portion 62 housing the actuator which contains the needle is disposable. FIG. 6A shows the portions 64 and 62 separate from each other as they would be immediately prior to use. Thus normally the reusable portion would have its open left hand end closed by a removable reusable cap (not shown.)

The reusable portion 64 consists of a barrel 82 having at its closed end a well 32 of reduced diameter in which a spring 16 is secured around a cylindrical back stop 84 which extends out beyond the end of the well into an actuator chamber 21 thus leaving an annular space 25 as in the FIG. 1 embodiment into which the end of the actuator can travel after the device has "fired".

Attached to the end of the spring 16 is an open ended cylindrical holder for the needle assembly. The outer peripheral edge of the holder 88 has a chamfer 89. The needle holder in the null position of the spring is located with its open end just inwards of the end of the barrel 82.

The disposable portion 62 consists of a hollow cylindrical actuator 68 having one end closed by a finger guard plate 78 in which there is a central aperture 80 through which the needle is driven in use. Prior to use this end is closed by a cap 72. The other end of the actuator is open except that for a distance L1 from its end it has an increased wall thickness, the cylindrical internal diameter in this stop region 76 being slightly greater than the external diameter of the needle holder 88 so as to act as a guide for it. The guiding function of the stop region 76 is enhanced by a chamfer 95 formed on the inside edge end 77 of the actuator 68. The stop region affords an axially disposed inwardly directed stop surface 74 to which a needle assembly 70 is secured prior to "firing" of the device.

Figure 6B:
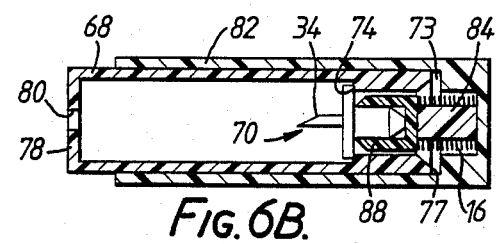
Figure 6C:
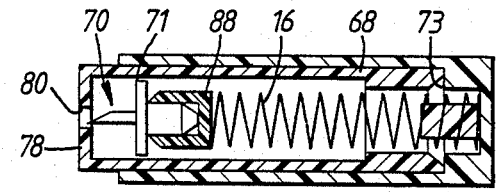

The needle assemble has a needle 34, a disc shaped transverse base 18 (with a cylindrical outer edge 71 spaced a significant distance from the inside wall of the actuator 68 so as to avoid air piston effects), and a much thickened shank 90 sized so as to be a close sliding fit in the needle holder 90 and provided with a chamfer 91 so as to guide engagement of the needle holder. The fit has to be tight enough to ensure that the needle is held in the holder sufficiently to be retracted back into the actuator after firing but no so tight as to prevent ready disengagement to permit disposal of the cartridge after use without damage to the spring 16. The rear face of the base plate (disposed towards the shank 90) is heat sealed, ultrasonically welded or otherwise releasably secured to the stop surface 74 in such a manner that the bond will be maintained whilst the spring 16 is being cocked but will be broken once the base of the needle holder 88 engages the backstop 84 (the moment of engagement being shown in FIG. 6B). As can be seen from FIG. 6B the length L1 of the stop region 76 is such that when the condition of FIG. 6B is reached the free end 77 of the stop region can still move into the annular region 25 before engaging the inner end wall 73 of the actuator chamber. It is this movement that breaks the connection between the rear face of the base 18 and the stop surface 74 releasing the spring 16 and "firing" the device. Once this has occured the actuator can move freely further inwardly till its end 77 engages the wall 73 (as shown in FIG. 6C). FIG. 6C shows the device with the spring in the resting or null position after the pricking operation has been carried out.

Figure 6D:
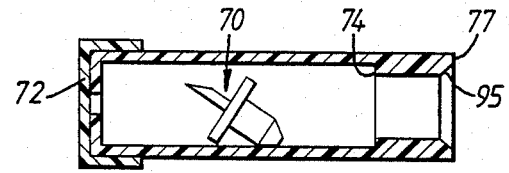

FIG. 6D shows the disposable portion 62 ready to be discarded indicating how the used needle is retained within the disposable portion.

If the rear face of base 18 is sealed continuously right round through 360° to the surface 74 and the cap 72 is sealed to the actuator it will be appreciated that the needle 34 can be sterilised and maintained sterile prior to use.

Thus in use the cap 72 is removed and the disposable portion is inserted into the reusable portion, the shank 90 resting in the holder. This commences "cocking" of the device, which is now located with the finger to be pricked against the hole 80 and the thumb on the other end of the barrel 82. The device can be cocked and fired in a single continuous application of pressure between finger and thumb. Again many variations are possible, the device used need not be cylindrical in cross section, other stop mechanisms can be used and other trigger mechanisms.

Instead of the seal between the base 18 of the needle assembly and the surface 74 being continuous it could be discontinuous and sterile conditions for the needle could be assured prior to use by a second cap 99 (not shown) removably sealed over the end 77 of the actuator.

In this arrangement simpler means could be used for holding the needle assembly till "cocking" had been achieved. The portion 76 could be a push fit on the remainder of the barrel 68 (or vice versa) and the inside face of the barrel 68 could afford protrusions either separately or as an annular rib or flange to hold the base of the needle until cocking has been achieved. Flange/base profiles as discussed for FIG. 1 could be used.

The second cap 99 would have to be sealed still to the barrel 68 to ensure a sterile environment for the needle prior to use. In a variation of this modification the barrel 68 could have the same cross section throughout its length, the stop function of the surface 74 being provided by small protruberances, or an annular flange, past which the needle assembly could be pushed so as to prevent it falling out of the end 77 after use.

As the finger guard 78 of the disposable portion 62 always lies beyond the open end of the barrel 82 of the re-usable portion 64, there is little chance of the reusable portion becoming contaminated, and it may be safely re-used with another disposable portion.

All the embodiments described afford the advantages of a cheap sterile assembly prior to use, a single movement being needed to use the device, and automatic retraction of the needle back within a substantially closed housing immediately after use thus substantially reducing the risk of cross contamination or recontamination. The simplicity and cheapness of the devices makes them economically practical for use as disposables.

What is claimed is:

1. A lancet device comprising:
   (a) a needle assembly having a lancet needle suitable for piercing human or other animal tissue;
   (b) means defining a housing containing said lancet needle, said housing having a substantially closed front end wall with a first aperture therein, and an abutment surface in spaced relation with the end wall;
   (c) sealing means for sealing said first aperture prior to operation of the lancet device;
   (d) a single firable biassing spring positioned within said housing, said spring being capable of being under compression or tension, said spring having a first end in abutment with the lancet needle and a second end in abutment with the abutment surface in the housing opposite said front end wall and being freely extendable between the first and second ends thereof to move the lancet needle from a first position within said housing to a second position in which said lancet needle at least partially protrudes out of said housing through said first aperture to pierce the human or other animal tissue;
   (e) means for initially retaining said single firable biasing spring under compression within the housing to hold said needle; and
   (f) means for releasing the firable biasing spring from the retaining means to allow the lancet needle to move to the second position wherein, when said lancet is in said second position, said biasing spring is in over-extension under tension, and said biasing spring relaxes from being under tension so as automatically to retract said lancet needle from said second position to a location within said housing.

2. The lancet device of claim 1, wherein the single firable biasing spring is a coil spring having a plurality of coils about axis aligned with the first apparatus in the front end wall and wherein the coils are free of any radial obstruction therebetween from the first to the second end of the spring.

3. The lancet device of claim 2, wherein there is a second aperture in a rear wall of the housing adjacent to the abutment surface and wherein the releasing means includes an end cap fittable over the substantially closed front end wall with the first aperture therein to form the sealing means therefore, the end cap having a projection thereon which is receivable in the second aperture upon removing the end cap from the front end wall and placing the end cap adjacent the second aperture, wherein the projection releases the firable biasing spring from the retaining means upon being inserted through the second aperture.

4. The lancet device of claim 3, wherein the retaining means comprises a stem on the lancet needle which is received in and frictionally retained in the second aperture so as to be selectively releasable therefrom by the projection extending from said end cap.

5. The device of claim 4, wherein the second aperture has means projecting thereinto which cooperates with shoulder means on the stem to frictionally retain the stem in the second aperture.

6. The device as claimed in claim 1 including a closure cap for closing the aperture said closure cap including the means for releasing the retaining means.

7. A device as claimed in claim 1 comprising two components in relatively slideable relationship and arranged to be squeezed together to release the retaining means.

8. A device as claimed in claim 7 in which the needle assembly is connected to one of the two said components, and the connection is broken to initiate release of the retaining means.

9. A device as claimed in claim 7 in which the two said components comprise a barrel and an actuator carrying the spring means, which components are arranged to slide telescopically together in an axial direction.

10. A device as claimed in claim 9 in which the two components are spaced in the axial direction from one another before being squeezed together to release the retaining means

* * * * *